US00PP36084P2

(12) United States Plant Patent
Rupp

(10) Patent No.: US PP36,084 P2
(45) Date of Patent: Aug. 27, 2024

(54) ***DIANTHUS* PLANT NAMED 'KLEDG22448'**

(50) Latin Name: ***Danthus caryophyllus* L.**
Varietal Denomination: KLEDG22448

(71) Applicant: KLEMM + SOHN GMBH & CO. KG, Stuttgart (DE)

(72) Inventor: Judith Rupp, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 18/214,359

(22) Filed: Jun. 26, 2023

(51) Int. Cl.
*A01H 5/02* (2018.01)
*A01H 6/30* (2018.01)

(52) U.S. Cl.
USPC ..... Plt./277
CPC ..... *A01H 6/305* (2018.05)

(58) Field of Classification Search
USPC ..... Plt./282, 277
CPC ..... A01H 5/02
See application file for complete search history.

(56) References Cited

PUBLICATIONS https://selecta-one.com/katalog/catalogs/Dianthus-ESC-NE-22-23/pdf/complete.pdf; Oct. 6, 2023; 2 pages.*

* cited by examiner

*Primary Examiner* — Kent L Bell
(74) *Attorney, Agent, or Firm* — Weatherly IP Solutions, LLC; James M. Weatherly

(57) ABSTRACT

A new *Dianthus* plant designated 'KLEDG22448' particularly distinguished by single, purple-pink flowers with a macule type pattern, entire petal margins, and winter hardy, is disclosed.

1 Drawing Sheet

Genus and species: *Dianthus caryophyllus* L.
Variety denomination: 'KLEDG22448'.

BACKGROUND OF THE NEW PLANT

The present invention comprises a new and distinct variety of *Dianthus*, botanically known as *Dianthus caryophyllus* L., and hereinafter referred to by the variety name 'KLEDG22448'. 'KLEDG22448' originated from an open cross pollination from the proprietary female parent 'DSS-2016-0163' (unpatented) and an unknown male parent in 2017 between May and August in Stuttgart, Germany.

A plant line was selected in May 2018 in Stuttgart, Germany, and named 'KLEDG22448'. In June 2018, 'KLEDG22448' was first vegetatively propagated by vegetative cuttings in Stuttgart, Germany. 'KLEDG22448' was found to reproduce true to type in successive generations of asexual propagation in Stuttgart, Germany via vegetative cuttings.

SUMMARY

The following are the most outstanding and distinguishing characteristics of 'KLEDG22448' when grown under normal horticultural practices in Stuttgart, Germany.

1. Single, purple-pink flowers with a macule type pattern;
2. Entire petal margins; and
3. Winter hardy.

DESCRIPTION OF THE PHOTOGRAPH

This new *Dianthus* plant is illustrated by the accompanying photograph of a 12-week-old plant taken in September 2022 and grown indoors in Stuttgart, Germany. The colors shown are as true as can be reasonably obtained by conventional photographic procedures. The photograph is a whole plant photo of 'KLEDG22448' and shows the foliage, buds, and flowers.

DESCRIPTION

The following detailed descriptions set forth the distinctive characteristics of 'KLEDG22448'. The data which define these characteristics were collected from asexual reproductions carried out in Stuttgart, Germany. Data was collected in April 2023 from plants 30 weeks from potting on plants that were potted in October 2022 and grown in a plastic greenhouse. Color references are to The R.H.S. Colour Chart of The Royal Horticultural Society of London (R.H.S.), $5^{th}$ edition (2007).

Classification:
- *Family*.—Caryophyllaceae.
- *Botanical*.—*Dianthus caryophyllus* L.
- *Designation*.—'KLEDG22448'.
- *Type*.—Pot carnation.

Parentage:
- *Female parent*.—'DSS-2016-0163' (unpatented).
- *Male parent*.—Unknown.

Plant:
- *Propagation type*.—Vegetative cuttings.
- *Time to produce a rooted young plant*.—28 days.
- *Root description*.—Fine; roots, color is white, RHS 155A.
- *Rooting habit shape*.—Lanceolate.
- *Plant form*.—Upright.
- *Plant height*.—13.0 cm.
- *Plant diameter or spread*.—20.0 cm.

Lateral branches/stems:

*Shape of the branch in cross-section*.—Circular.
*Hollowness of the branch*.—Absent.
*Length*.—11.0 cm.
*Diameter*.—0.2 cm.
*Stem thickness*.—Medium.
*Internode length*.—3.5 cm.
*Internode quantity per branch*.—4.
*Number of internodes per branch/stem*.—4.
*Node length*.—0.5 cm.
*Node diameter*.—0.3 cm.
*Texture*.—Smooth.
*Color*.—RHS 137A.
*Flower clustering on the lateral branch*.—In some lateral branches.

Foliage:

*Arrangement*.—Opposite.
*Length*.—6.0 cm.
*Width*.—0.4 cm.
*Shape*.—Linear.
*Apex*.—Narrowly acute.
*Base*.—Round.
*Margin*.—Entire.
*Texture* (*both upper and lower surfaces*).—Smooth.
*Cross-section of the leaf*.—Weakly concave.
*Curvature of the leaf*.—Absent.
*Glaucosity of the leaf*.—Medium.
*Leaf color* (*both immature and mature*).—Immature: Upper surface: RHS 137A. Lower surface: RHS 137A. Mature: Upper surface: RHS N137A. Lower surface: RHS 137A.
*Venation pattern*.—Absent.

Flowers:

*Flower type*.—Single.
*Fragrance*.—Absent.
*Position of the flowers compared to the foliage of the plant*.—Same level.
*Profile of both the upper and lower part in the lateral view*.—Flat convex.
*Diameter of the flower*.—3.7 cm.
*Natural flowering season*.—Spring to Autumn.
*Number of flowers per spray*.—2 to 3.
*Flower longevity on the plant*.—14 days.

Buds:

*Length*.—2.5 cm.
*Diameter*.—0.6 cm.
*Shape*.—Oblong.
*Color*.—RHS N187C.
*Extrusion of the styles at the bud stage*.—Absent.

Corolla:

*Quantity of petals and arrangement*.—6 and arranged in several whorls.
*Corolla height*.—1.0 cm.
*Petal length*.—2.3 cm.
*Petal width*.—1.9 cm.
*Petal shape*.—Obovate.
*Petal apex*.—Obtuse.
*Petal base*.—Acute.
*Petal margin*.—Entire.
*Depth of petal margin*.—Shallow.
*Petal texture* (*both upper and lower surfaces*).—Smooth.
*Petal color*.—Immature: Upper surface: RHS N78A. Lower surface: RHS 72B. Mature: Upper surface: RHS 72B. Lower surface: RHS N78B.
*Macule*.—Present RHS 71A.
*Macule size*.—0.3 cm to 0.4 cm at the single petal.

Calyx:

*Quantity of sepals*.—Composed of 5 sepals.
*Longitudinal axis of the lobes of the calyx*.—Straight.
*Shape*.—Cylindrical.
*Calyx height*.—1.8 cm.
*Calyx diameter* (*at the apex*).—0.6 cm.
*Sepal texture* (*both upper and lower surfaces*).—Smooth.
*Sepal color*.—Upper surface: RHS N137B. Lower surface: RHS 138B.
*Position of the outer lobes of the epicalyx in relation to the calyx*.—Adpressed.
*Apex shape of the outer lobes of the epicalyx*.—Short acuminate.
*Tip length of the outer lobes of the epicalyx*.—2.2 cm.
*Apex shape of the inner lobes of the epicalyx*.—Medium acuminate.
*Tip length of the inner lobes of the epicalyx*.—1.3 cm.

Peduncles:

*Length*.—3.0 cm.
*Diameter*.—0.2 cm.
*Strength*.—Medium.
*Texture*.—Smooth.
*Color*.—RHS 138A.

Reproductive organs:

*Stamens*.—Quantity per flower: 10. Filament length: 0.6 cm. Filament color: RHS 145D. Anther length: 0.1 cm. Anther diameter: Less than 0.1 cm. Anther color: RHS 153D. Pollen amount: None observed.
*Pistils*.—Quantity per flower: 2. Length: 0.9 cm. Diameter: 0.1 cm. Stigma: Color: RHS N81A. Shape: Filamentous. Length: 0.1 cm. Diameter: Less than 0.1 cm. Style: Color: RHS NN155A. Length: 0.8 cm. Diameter: 0.1 cm. Number: Two. Style shoulder: Absent. Ovary: Color: RHS 145C. Width: 0.3 cm. Texture: Smooth with fine riffles at the base.

Fruit and seed set: None observed.

Disease and pest/insect resistance: No particular disease or insect resistance observed.

COMPARISON WITH PARENTAL LINE AND KNOWN VARIETY

'KLEDG22448' is distinguished from the parental line as described in Table 1.

TABLE 1

| Comparison with Parental Line | | |
|---|---|---|
| Characteristic | 'KLEDG22448' | Female Parent 'DSS-2016-0163' |
| Petal margin | Entire | Crenate-dentate |
| Flower pattern | Macule type | Eye |

'KLEDG22448' can be compared to the unpatented *Dianthus* variety 'KLEDP07089' (unpatented). Differences between the varieties are described in Table 2.

TABLE 2

| Comparison with Similar Variety | | |
|---|---|---|
| Characteristic | 'KLEDG22448' | 'KLEDP07089' |
| Flower color | Purple pink | Pink and purple pattern |
| Winter-hardy | Present | Absent |
| Flower | Single | Semi-double |

I claim:

1. A new and distinct cultivar of *Dianthus* Plant Named 'KLEDG22448' as described and illustrated herein.

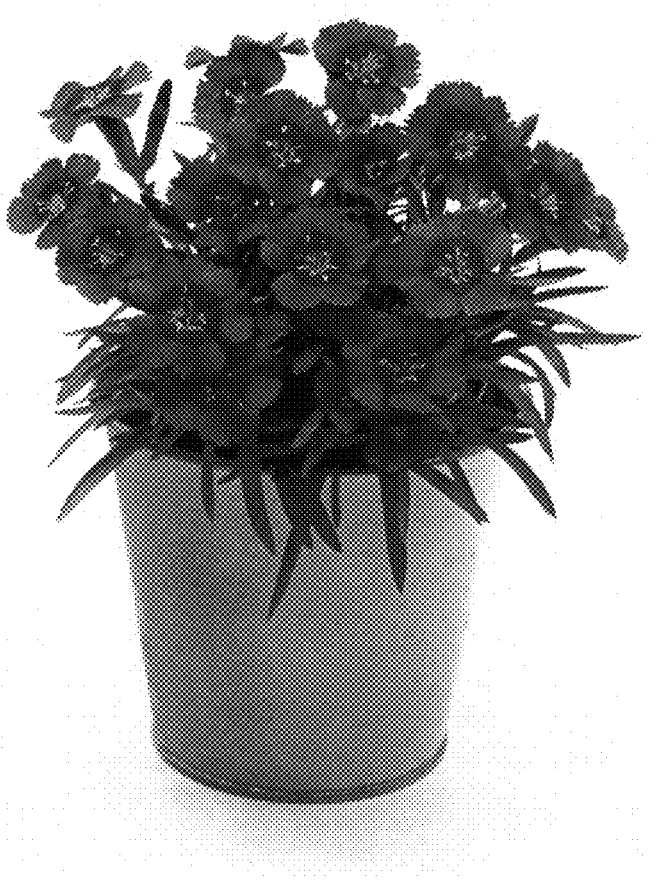

* * * * *